(12) United States Patent
Molnár et al.

(10) Patent No.: US 8,203,575 B2
(45) Date of Patent: Jun. 19, 2012

(54) METHOD AND SYSTEM FOR ACCESSING A SLIDE FROM A REMOTE WORKSTATION

(75) Inventors: Béla Molnár, Budapest (HU); Viktor Sebestyén Varga, Budapest (HU); Attila Tagscherer, Tiszadorogma (HU)

(73) Assignee: 3DHistech KFT., Budapest (HU)

( * ) Notice: Subject to any disclaimer, the term of this patent is extended or adjusted under 35 U.S.C. 154(b) by 1020 days.

(21) Appl. No.: 12/042,050

(22) Filed: Mar. 4, 2008

(65) Prior Publication Data

US 2008/0306964 A1   Dec. 11, 2008

(30) Foreign Application Priority Data

Jun. 11, 2007   (HU) ...................................... 0700409

(51) Int. Cl.
   *G09G 5/00*   (2006.01)
   *G06K 9/00*   (2006.01)
(52) U.S. Cl. ........................................ 345/629; 382/128
(58) Field of Classification Search ................... 345/629; 382/128
   See application file for complete search history.

(56) References Cited

U.S. PATENT DOCUMENTS

| 6,396,941 | B1 * | 5/2002 | Bacus et al. | 382/128 |
| 7,653,251 | B2 * | 1/2010 | Dei et al. | 382/232 |
| 2007/0282843 | A1 * | 12/2007 | Beck | 707/9 |

* cited by examiner

*Primary Examiner* — Ryan R Yang
(74) *Attorney, Agent, or Firm* — Jason D. Voight (57) ABSTRACT

The invention relates to a method for accessing a slide from a plurality of digitized microscope slides from a remote workstation, wherein the plurality of digitized microscope slides are accessible via a plurality of data station units (DSU), the method comprising:
  providing a central management station unit (CMSU) connected to a communication network for storing slide information of the plurality of digitized microscope slides,
  allowing the workstation to connect to the CMSU via the communication network;
  providing at least a part of the slide information of the plurality of digitized microscope slides to the workstation;
  allowing the workstation to select a digitized microscope slide based on the provided slide information; and
  allowing for a direct connection over the communication network between the remote workstation and a DSU enabling access to the selected digitized microscope slide.

The invention further relates to a system and a CMSU for carrying out the method.

30 Claims, 4 Drawing Sheets

METHOD AND SYSTEM FOR ACCESSING A SLIDE FROM A REMOTE WORKSTATION

BACKGROUND OF THE INVENTION

1. Field of the Invention

The present invention relates to a method and system for accessing a digitized microscope slide from a remote workstation, wherein a plurality of digitized microscope slides are stored in a plurality of data station units.

2. Background Art

The analysis of tissue sections is an important field of medical diagnostics. For conducting a tissue analysis the tissue specimen taken from a patient is sliced up in very fine sections (e.g. 2-10 µm thick sections), which are then placed on glass plates and are stained with various dyes. Finally, the slide bearing the resulting specimen is analyzed/examined with a microscope.

The efficiency of the analysis can be substantially enhanced by virtual slide imaging, where the specimen slides are first digitized and can be viewed and analyzed afterwards in a convenient manner by suitable software applications. Virtual slide imaging is becoming more and more widespread as it offers a higher degree of freedom compared to conventional live microscopy where microscope specimen slides are viewed in real time and are examined by a person viewing the slide. The digitized microscope slides allow for faster viewing (since the images are already captured), for annotation of the specimen regions of interest, for computerized analysis of the specimen (e.g. finding given type of cells, measuring their area, etc.) and for an unlimited number of reviewing for diagnostic or educational purposes.

Since the digitized microscope slides are stored in electronic files the possibility of transferring these files to and reviewing at a remote computer is at hand. However, the digitized microscope slides tend to be extremely large. The specimen slides are digitized by an imaging device, which generally comprises a camera coupled to a microscope. The field of view of the resulting optical system corresponds to a relatively small portion of the whole slide, therefore, in order to scan the whole slide, the slide is divided into fields corresponding to the field of view of the optical system and an image is captured of each field. The individual images called image tiles are then aligned (or "stitched" together as commonly referred to) in a software application to form a single continuous image of the specimen slide. For example, the useful (net) surface area of a slide can be 25 mm by 50 mm. Applying a commonly used resolution of 0.3 µm, this means approximately 83 000 by 166 000 pixels. If each pixel is represented on 3 bytes, as is the standard practice, at a compression rate of 1:10, the size of the resulting file would still be 3.8 GB. The digitized microscope slides are usually stored in a plurality of files, however this does not reduce the overall data amount that has to be transferred if the slide is to be examined on a remote computer.

A further aspect to be taken into account when creating a digitized microscope slide is to allow for conventional type of slide examination, which implies viewing the digitized microscope slide at different magnifications. In conventional live microscopy the examining pathologist first examines the specimen slide using a low magnification objective in order to gain an overall view of the specimen and possibly to locate regions of interest, which he then reviews using a higher magnification objective. Conventional microscopes can have three or even more different magnification objectives, it is therefore required to allow for reproducing at least these magnifications in virtual microscopy as well. This is usually done by down-scaling the images taken with a high-resolution, high-magnification objective. For example, in order to display an image captured using an objective of 20× magnification as if it were taken using an objective of 4× magnification, the image is to be reduced digitally at a rate of 5:1 in both directions x and y. However the image viewing application must still handle a file that is twenty-five times larger than the one actually needed, which can lead to unacceptable deceleration. The commonly used solution is to down-scale the images during or after the digitization and store the images at a plurality of different magnifications, thus a single digitized microscope slide generally comprises images of the specimen slide at a number of different magnifications.

The size and number of files can further increase in the case of fluorescent microscopy. Most image formats store a maximum of three color channels, however in the case of fluorescent microscopy a number of different fluorescent filters may be applied for viewing the same specimen slide at a number of different wavelengths resulting in further data amount.

Moreover, with the spreading of Internet there is an ever-growing demand for transferring or viewing digitized microscope slides over the Internet. A similar desire can arise in the case of computers connected by Intranet, or a local area network (LAN) for example in a hospital or a research institute where the specimen slides are being digitized by a computer controlled camera coupled to a microscope and are to be viewed and examined by a pathologist working with another computer. The commonly used solution is to store the digitized microscope slides in a central computer or server accessible by a number of remote workstations connected to the central computer by a communication network (Internet, Intranet, LAN or any other communication network), thus all or part of the images of a digitized microscope slide can be downloaded or viewed over the communication network.

U.S. Pat. Appl. No. 2006/0188137 discloses a method and an apparatus for viewing digitized microscope slide images including transmitting image tiles of the slide from a central server to a remote client. The client assembles the tiled images into a seamless virtual slide and provides tools for manipulating image magnification and viewpoint.

Making use of a single server for storing the digitized microscope slide can lead to very high bandwidth requirements, especially if a large number of clients are likely to request viewing or downloading of files simultaneously.

It would also be desirable to view digitized microscope slides located on not just one server but rather on a plurality of servers or computers, for example on servers run by different hospitals or research institutes or personal computers of doctors or members of a research team.

SUMMARY OF THE INVENTION

Present systems do not allow for an integrated handling of digitized microscope slides stored at different locations. A user may have access to a number of separate servers storing digitized microscope slides, however in order to find slides of a specific criteria the user must connect to all servers and search their databases one by one, which is an inconvenient, time consuming process.

It is therefore a first objective of the invention to eliminate the drawbacks of the prior art solutions.

It is another object of the present invention to lower the bandwidth requirements of a network and provide more equalized network traffic for viewing or downloading digitized microscope slides from a remote location by providing access to a plurality of data station units storing digitized microscope slides or having access to digitized microscope slides, and at the same time eliminating the drawback of having to access and search the data station units separately.

These objects are achieved by providing a method for accessing a slide from a plurality of digitized microscope slides from a remote workstation, wherein the plurality of digitized microscope slides are accessible via a plurality of data station units (DSU), the method comprising providing a central management station unit (CMSU) connected to a communication network for storing slide information of the plurality of digitized microscope slides, allowing the workstation to connect to the CMSU via the communication network;

providing at least a part of the slide information of the plurality of digitized microscope slides to the workstation;

allowing the workstation to select a digitized microscope slide based on the provided slide information; and allowing for a direct connection over the communication network between the remote workstation and a DSU enabling access to the selected digitized microscope slide.

The invention further relates to a system for accessing a slide from a plurality of digitized microscope slides from a remote workstation connected to a communication network, the system comprising a plurality of data station units (DSU) connected to the communication network and each having access to at least one of the plurality of digitized microscope slides;

a central management station unit (CMSU) connected to the communication network and configured to:

obtain slide information of the plurality of digitized microscope slides from the plurality of DSUs;

provide the remote workstation with at least part of the slide information over the communication network;

allow the remote workstation to select a digitized microscope slide based on the provided slide information; and allow for a direct connection over the communication network between the remote workstation and a DSU having access to the selected digitized microscope slide.

The invention further relates to a central management station unit (CMSU) connected via a communication network to a plurality of remote workstations and to a plurality of data station units (DSU) having access to a plurality of digitized microscope slides, wherein the CMSU is configured to store slide information of the plurality of digitized microscope slides, and provide the remote workstation with at least part of the slide information over the communication network.

Further details of the invention will be apparent from the accompanying figures and exemplary embodiments.

DETAILED DESCRIPTION OF THE PREFERRED EMBODIMENTS

Figure 1:
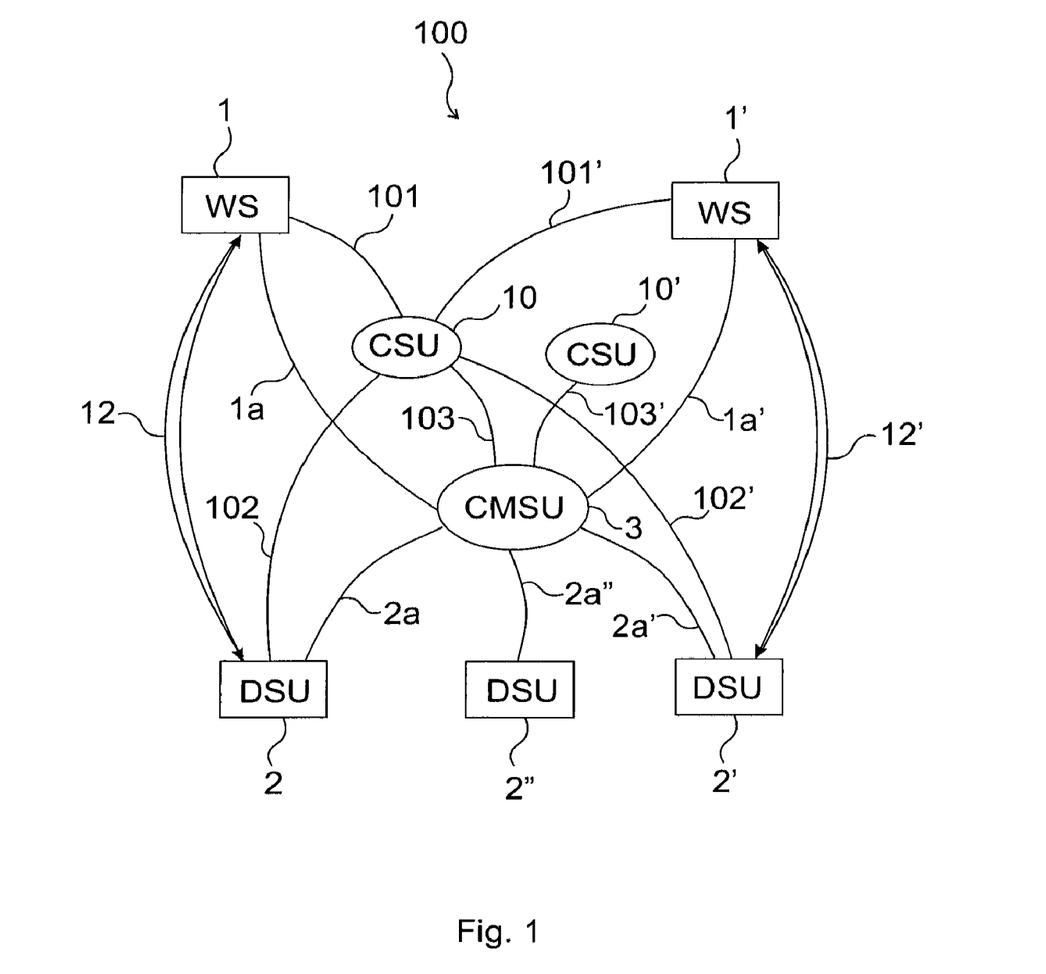
FIG. 1 is a block diagram illustrating the operation of a system according to the invention.

FIG. 1 illustrates the operation of a first exemplary embodiment of a system 100 according to the invention. A plurality of workstations (WS) 1, 1' and a plurality of data station units (DSU) 2, 2', 2" are connected via communication lines 1a, 1a' and 2a, 2a', 2a" respectively to a central management system unit (CMSU) 3. The communication lines 1a, 1a' and 2a-2a" are preferably network lines in a communication network, which can be for example Internet, Intranet, LAN, or any other communication network suitable for exchanging information thereover. Although only a small number of workstations 1, 1' and DSUs 2-2" are depicted in the figure, it is clear that any number of workstations and DSUs are conceivable, also, there is usually no relationship between their respective numbers.

A direct connection can be established between a workstation 1, 1' and a DSU 2-2" for downloading files from the DSU 2-2". Such direct connections are communication lines 12, 12' in FIG. 1.

Further, in the depicted embodiment two communication server units (CSU) 10, 10' are connected to the CMSU 3 and the workstations 1, 1' via communication lines 103, 103' and 101, 101' respectively. The CSU 10, 10' can furthermore establish connection to a DSU 2-2" as well via communication lines 102, 102'.

The preferred number of CSUs 10, 10' may vary depending on the size of the system 100. For example, in the case of a small system 100 (e.g. used by less than fifty user workstations 1, 1') a single CSU 10, 10' might be sufficient, whereas in case of larger systems 100 (e.g. serving hundreds of user workstations 1, 1') two, three or even more CSUs 10, 10' might be required as will be apparent from the following description.

The CMSU 3, the DSUs 2-2", and CSUs 10, 10' can either be physical units such as a server; or logical units such as a software application that can be installed on a server. In the later case it is not excluded to install more than one logical units on the same server, for example both a CMSU 3 and a DSU 2-2", or both a CMSU 3 and a CSU 10, 10' can be hosted on the same physical entity (e.g. server), which can then function as two different logical entities at the same time (CMSU and DSU or CMSU and CSU, respectively, in the example). In the following description the CMSU 3, the DSUs 2-2" and the CSUs 10, 10' will be referred to as physical servers comprising the software application CMSU, DSU and CSU, respectively, not excluding the possibility that any two or even all three servers may coincide.

In the embodiment shown in FIG. 1 a plurality of digital microscope slides are stored in the DSUs 2-2" and can be accessed by a user from the workstation 1, 1' via the intermediate CMSU 3. In the context of the invention accessing the digitized microscope slides is used in a broad sense comprising viewing, manipulating, downloading the digitized microscope slides or reading, writing the respective files, or any other action or operation that can be carried out with the digitized microscope slides.

Accessing a digital microscope slide via the embodiment of FIG. 1 is carried out in the following way.

In this exemplary embodiment it is conceived that a plurality of digital microscope slides are stored in the plurality of DSUs 2-2". Some of the slides may be stored in a single DSU 2-2", other ones may be stored in more than one DSU 2-2".

A user at workstation 1 wishes to view or download a digitized microscope slide stored in one or more DSUs 2-2". To do this the user first connects to the CMSU 3 via the communication line 1a provided between the workstation 1 and the CMSU 3. It should be noted that the communication lines 1a, 1a' and 2a-2a''' are rather virtual lines than invariable physical lines, for example if the communication network is the Internet, the communication between workstation 1 and CMSU 3 may actually take place over different Internet lines and nodes each time. For example, the workstation 1 is understood to cover mobile workstations such as a laptop, palmtop, etc., in which case it is very likely that the workstation 1 would be using different networks, including wireless networks, to connect to the Internet. However, for the sake of simplicity the established communication channel will always be referred to by communication line 1*a* independent of the physical realization of the channel.

Once the connection has been established (for example by visiting the appropriate website of the CMSU 3) advantageously a user identification can take place to define the rights of the user, for example to define what kind of information the user is entitled to have access to.

For the purpose of determining user rights the method according to the invention advantageously comprises providing user identification means for the user at the workstation 1 by the CMSU 3 and later on verifying the user identification means when the workstation 1 requests data from a DSU 2 storing the selected digitized microscope slide. In practice the user could log on to the CMSU 3 and obtain user identification means depending on the user's status. For example, the user could be a registered member having access to all of the digitized microscope slides and entitled to make annotations, or the user could be a registered member with limited rights having an access to all of the digitized microscope slides but lacking the right to make annotations, or the user could be a guest having access to a limited number of digitized microscope slides, etc. The CMSU 3 provides the user with the user identification means indicative of the user rights associated with the user. The user identification means could be a code or a cookie, for example. This user identification means is then transmitted to a selected DSU 2 when the user wishes to access the selected digitized microscope slide stored in the DSU 2. The DSU 2 will use the provided user identification means for determining the user rights associated therewith, but may also check the validity of the identification means by sending it back to the CMSU 3 for confirmation. According to an advantageous embodiment, the verification comprises the steps of transmitting the user identification means from the DSU 2 to the CMSU 3 and requesting the verification of the user identification means, which generally implies verification of the validity of the user identification means, or the user rights associated with the user identification means.

After the user identification has taken place the CMSU 3 sends slide information authorized for the user, which could be displayed by a local browser program, preferably by a custom made viewer program installed on the workstation 1.

The slide information advantageously comprises at least one of the following: slide name, slide size, slide attributes, slide location, slide path, information identifying the DSU, information relating to a specimen on the slide, SNOMED code (Systematized Nomenclature [of Human and Veterinary] Medicine code), preview image of the slide, information relating to the proprietor of the slide.

In practice, the CMSU 3 could send slide information concerning the name and location of the slide (e.g. DSU identifying information such as an IP address, or a geographical location of the DSU 2, or the name of the institute hosting the DSU 2, or the like) and information relating to the type of the digitized microscope slide (e.g. the widely used SNOMED code of the tissue specimen). The CMSU 3 could provide practically any kind of slide information associated with the digitized microscope slides stored in the plurality of data servers 2-2''', for example the ones previously discussed.

Depending on the user rights, the CMSU 3 could for example provide access to a directory listing all the possible digitized microscope slides where all, or only a part of the slide information are visible. For example, the slide name and the SNOMED code of the slide could be displayed allowing a user at the workstation 1 to find a digitized microscope slide of interest. As will be explained later on the digitized microscope slides generally comprise a plurality of files, thus it is also possible to allocate a folder to each digitized microscope slide and list all the respective files, showing their size, attributes, etc. within the folder. In this case slide name, slide size, etc. can comprise the name, size, etc. of each file.

The method according to the invention preferably comprises searching for the slide information stored in the CMSU 3 based on at least one search criterion provided by the workstation 1 (i.e. a user at the workstation 1) and providing the workstation 1 with the slide information corresponding to the search criteria. For example, a user could be looking for digitized microscope slides with a given SNOMED code for research or educational purposes. In this case the search criterion is the desired SNOMED code and the slide information corresponding to the search criterion could be a list with slide information related to all the digitized microscope slides having the given SNOMED code. The user could then select one or more digitized microscope slides from the list and access these slides once a communication has been established between the workstation 1 and the appropriate one or more DSUs 2-2" storing the selected digitized microscope slides.

As explained before, the same digitized microscope slide may be stored in a plurality of DSUs, for example on DSU 2 and 2'. The user could determine manually, which DSU 2, 2' to access, for example by choosing the DSU 2 located closer to the workstation 1 (in terms of the communication network), for example a user located in Hungary will normally choose a DSU located in Europe instead of one in the US.

Alternatively, the viewer program could select the DSU 2 automatically, for example by testing the speed of communication between each available DSU 2, 2'. This is preferably done by testing the communication bitrate for each provided DSU address of each DSU 2, 2' storing the selected digitized microscope slide and selecting a DSU address depending on the obtained communication bitrates, which normally implies selecting the DSU 2, 2' with the fastest communication channel.

Alternatively, the CMSU 3 could allocate a DSU 2 to the workstation 1, for example by designating the DSU 2 with the least actual workload in order to achieve a balanced network load for optimizing the overall performance and efficiency of the system 100, or in any other practical way.

Once a DSU 2 has been chosen for the purpose of serving the workstation 1, a direct communication line 12 is established between the DSU 2 and the workstation 1. If the user identification involved providing the workstation 1 with a user identification means, for example a cookie, this cookie itself could be sent to the DSU 2 which would then verify the user rights by requesting the user right information associated with the cookie from the CMSU 3. Alternatively, the DSU 2 could be in the position to determine the user rights from the cookie or from any other user identification means. After this step the DSU 2 can allow access to the requested digitized microscope slide. Depending on user rights, this could comprise viewing, downloading, modifying, annotating, or any other way of manipulating the selected digitized microscope slide.

Figure 2:
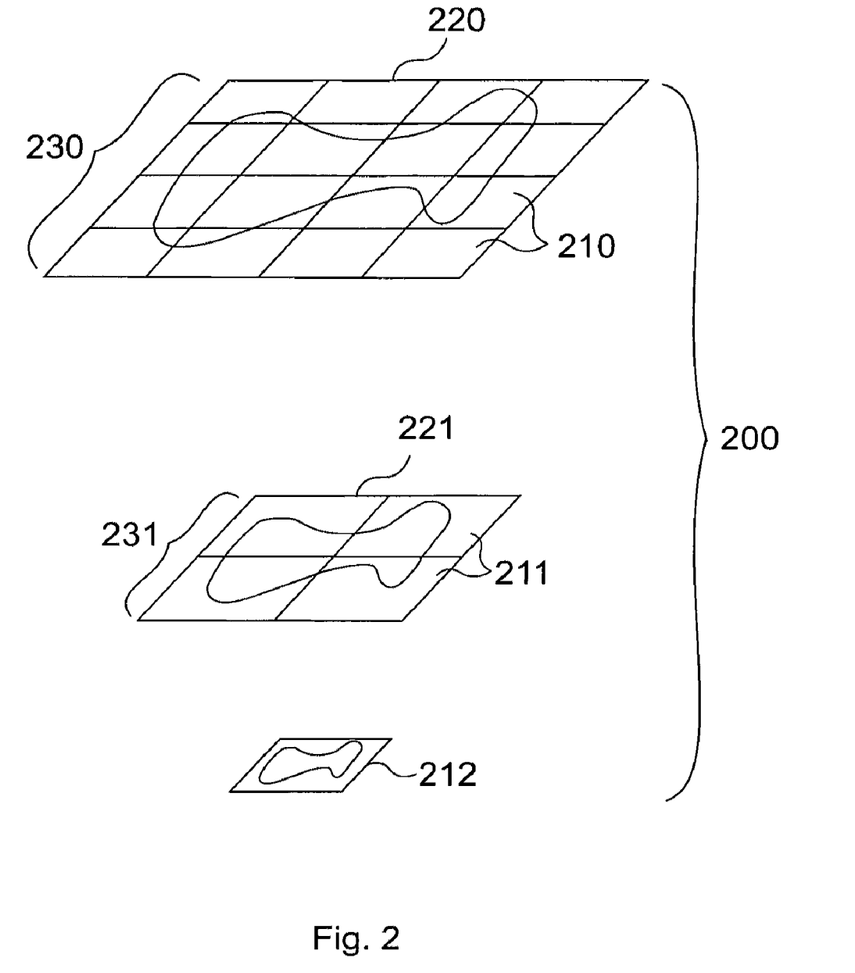
FIG. 2 is an illustrative diagram of different magnifications of a digital microscope slide.

The digitized microscope slides 200 of a preferred embodiment of the invention will now be presented with reference to FIG. 2.

As explained before, the digitized microscope slide 200 generally comprises a large number of different magnification image tiles 210, 211, 212 that can be aligned (stitched together) to form different magnification composite images 220, 221 of the original microscope specimen slide. The use of image tiles results from digitizing the specimen slide via an imaging system having a much smaller field of view than the area of the specimen slide.

As illustrated in FIG. 2 the digitized microscope slide 200 preferably comprises sets 230, 231 of image tiles 210, 211 each image tile set 230, 231 corresponding to a composite image 220, 221 of the microscope specimen slide at a given magnification. The digitized microscope slide 200 further comprises aligning information (not shown) for aligning the image tiles 210, 211 of a set 230, 231 to form a seamless, composite image 220, 221, respectively, of the specimen slide at a given magnification. Storing a plurality of image tile sets 230, 231 of different magnifications reduces the data amount to be handled when viewing the specimen at a lower magnification; instead of having to transfer a large number of high magnification image tiles 210 to the workstation 1, align them, and down-scale them via a viewer program to show a specific region of the specimen at a lower magnification, the user can simply download the one or few lower magnification image tiles 211 corresponding just to the region of interest.

Preferably, a single image tile 212 forms the lowest magnification image of the specimen slide. This image tile 212 is preferably used as a thumbnail image of the specimen slide and could be provided by the CMSU 3 along with other slide information of the digitized microscope slide 200 to a user at the workstation 1, 1' when searching for the slide information.

The image tiles 210, 211, 212 can either be captured by using a plurality of microscope objectives having different magnifications/resolutions or they can be captured by a single high magnification/resolution objective and be down-scaled digitally to create smaller magnification image tiles 211, 212. Note, that in the latter case it is very easy to find respective image tiles 210, 211, 212 of different magnifications, since a certain number of higher magnification image tiles 210 were used to create the lower magnification image tiles 211, 212 (in the present example four higher magnification image tiles 210 are used to create a single lower magnification image tile 211 and again four lower magnification image tiles 211 are used to create a single thumbnail image 212). This allows for easy zooming in and out between the different magnifications, whereas if the image tiles of each set 230, 231 are captured with a different objective, then the image tiles of different magnifications have to be mapped to each other, since the imaging device has different fields of view at the different magnifications.

It should also be understood that different magnifications may include different resolutions as well, particularly if the image tiles 210, 211, 212 are captured using different objectives.

Preferably, the method comprises requesting one or more image tiles 210, 211, 212 of a given magnification of the selected digitized microscope slide 200 from the DSU 2 storing the digitized microscope slide 200, and transmitting the requested image tiles 210, 211, 212 and aligning information for aligning the image tiles 210, 211, 212. Preferably, a viewer program is provided at the remote workstation 1 for sending the request and aligning the transmitted image tiles 210, 211, 212 on the basis of the transmitted aligning information and for displaying a region of the microscope specimen slide using the aligned image tiles 210, 211, 212. The viewer program can be a custom made program, or an HTML browser or any other application commonly used for viewing data over a communication network, in particular over the Internet.

Preferably, only the image tiles 210, 211 constituting a region of interest are transmitted to the workstation 1. In this case the viewer program displays the region of interest and is preferably configured to request adjacent image tiles 210, 211 of the same magnification of the displayed region of the microscope specimen slide from the DSU 2 when the user scrolls out of the displayed region. In practice, this could mean that whenever the user wishes to scroll up/down or left/right, the viewer program determines from the aligning information which image tiles 210, 211 need to be displayed and requests these image tiles 210, 211 from the DSU 2.

Preferably, the viewer program is also configured to request image tiles 210, 211, 212 of another magnification when a user zooms in or out of the displayed slide region.

Preferably, the viewer program is also configured to cache the transmitted image tiles 210, 211, 212 for use when displaying the same slide region at the same magnification again.

The method according to the invention preferably comprises calibrating a display unit (e.g. a monitor) at the remote workstation 1.

Figure 3:
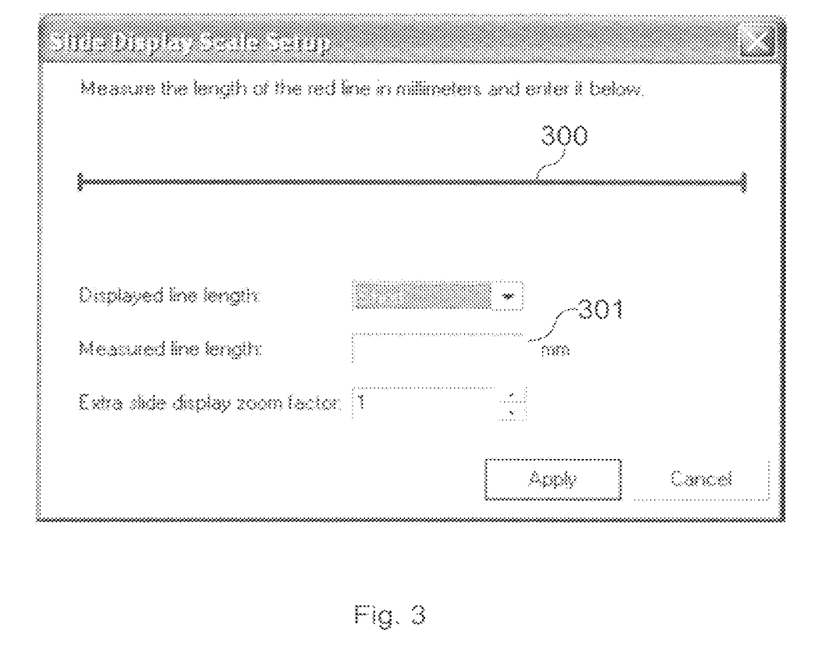
FIG. 3 is an image of a calibration window displayed by a viewer program.

Calibration is performed by providing the user at the workstation 1 with a calibration line 300, as can be seen in FIG. 3. This can be done for example via a custom made viewer program: a calibration line 300 is displayed on the display unit (monitor) of the workstation 1 via the viewer program and the user is required to measure the length of the calibration line 300 and return the measured value in given units (e.g. mm) by filling out the "Measured line length" field 301. The calibration line 300 is preferably made up of a given number of pixels in a straight horizontal or vertical line.

The calibration ensures that the image tiles 210, 211 displayed at the workstation 1 appear in a physical size corresponding to the required magnification of the specimen slide.

For example, the specimen slide is digitized using a 10× magnification objective coupled to a digital camera. The resolution of the objective-camera system is such that a 0.1 µm by 0.1 µm area corresponds to a single pixel of the captured image. Thus, for example a straight (horizontal or vertical) line of 1000 pixels of a 10× magnification image tile corresponds to a 100 µm (0.1 mm) long straight line on the original specimen slide. The monitor at workstation 1 can have a different resolution, for example a single pixel could be displayed in a size of 100 µm by 100 µm. When displaying the same straight line of 1000 pixels of the 10× magnification image tile, the 1000 pixels appear to form a 100 mm long line. Hence, the user at workstation 1 will be viewing the image of the original specimen slide at a 1000× magnification (or at a 100× magnification with respect to the slide as seen through the 10× microscope ocular) if the pixels of the image tile are displayed 1:1.

In order to display a given image tile in a given physical size irrespective of the used display unit, the viewer program uses the measured line length of the calibration line 300 for calculating the magnification of the display unit (display magnification) and for calculating a corrected magnification therefrom. For example the user at the workstation 1 wishes to view an image tile (or a plurality of image tiles) at 20× magnification. As explained above, the 20× magnification corresponds to a 200× magnification because of the 10× magnification microscope ocular. Thus, 1 pixel should appear in a length of 0.1 µm×200=20 µm. However, because a single pixel of the monitor is displayed in a length of 100 µm, the linear dimensions of the 10× magnification image tile would appear to be 5× greater (100 µm=5×20 µm), thus the 20× magnification image tiles need to be downscaled by 5:1 in both x and y directions.

The calculated corrected magnification can be used to automatically resize the image tile (e.g. downscale by 5:1 in the above example) or to request image tiles 210, 211 of a corresponding magnification from the DSU 2, 2' if available. The two methods can also be combined by requesting the magnification closest to the calculated corrected magnification and re-scale it to match the calculated corrected magnification exactly.

It is also possible to provide separate calibration lines 300 for the vertical and horizontal directions, which is particularly advantageous if the imaging system used for digitizing the original specimen slide had different magnifications along two perpendicular axis. The use of two calibration lines 300 is not discussed in further detail, as it will be apparent to a skilled person from the above examples.

Further, the method preferably comprises annotating the selected digitized microscope slide 200 by annotating at least one image tile 210, 211, 212 of a displayed slide region via the viewer program and transmitting the annotation back to the DSU 2. The annotations could be sent back to the DSU 2 immediately or they could be temporarily stored in the workstation 1 and transmitted back only at the end of the work session. The annotations could be stored in existing files or as new files. Whether the DSU 2 allows overwriting existing files or creating new files could depend on the user rights. Also, depending on user rights, a user may or may not have access to certain digitized microscope slides 200.

In parallel, a second user at a second workstation 2' may also wish to access the digitized microscope slide 200 selected by the first user at the first workstation 2. The second user goes through a similar procedure as described above and as a result can either be connected to the same (first) DSU 2 as the first workstation 1 or to a different (second) DSU 2' via a communication line 12' as shown in FIG. 1.

The method according to the invention preferably allows for teleconsultation as well, meaning that the more than one users viewing the same digitized microscope slide 200 simultaneously from different remote workstations 1, 1' are provided with the possibility of consulting with each other.

It is clear that all the embodiments relating to teleconsultation also apply to teleconsultation with the participation of more than two workstations. Nevertheless, for the sake of simplicity, the following preferred embodiment will only be discussed for two workstations 1, 1'.

A preferred method according to the invention can comprise providing the slide information of the digitized microscope slide 200 selected by the (first) remote workstation 1 to a second remote workstation 1'; and enabling a communication via communication line 12' between the second remote workstation 1' and a second DSU 2' storing the same selected digitized microscope slide 200.

The second DSU 2' being in communication with the second workstation 1' need not coincide with the first DSU 2 providing the selected digitized microscope slide to the first workstation 1. The method could allow for establishing a communication line 12 between the first workstation 1 and a first DSU 2, and establishing a communication line 12' between the second workstation 1' and a second DSU 2' both DSUs 2, 2' storing the selected digitized microscope slide 200, and communicating over a selected CSU 10 (as will be explained later) for viewing the same region of the selected digitized microscope slide 200 at the same magnification at both remote workstations 1, 1'. This is particularly advantageous in cases where the second workstation 1' would not have the same quality connection to the first DSU 2 providing the digitized microscope slide 200 to the first workstation. For example if the first workstation 1 is located in Europe and the second workstation 1' is located in the US, the first workstation 1 is advantageously connected to a first DSU 2, in Europe, while the second workstation 1' is advantageously connected to a second DSU 2' in the US.

When teleconsulting, the first and second users will generally wish to communicate with each other. Preferably, the communication between the first and second remote workstations takes place via a selected CSU 10 over communication lines 101 and 101', respectively. The CSU 10 can be selected similarly to the DSU 2. For example, the first user initiating the teleconsultation could select a CSU 10 manually from a list proposed by the CMSU 3, or the viewer program at the first workstation 1 could select an appropriate CSU 10 automatically based on a measured communication bitrate or the CMSU 3 could allocate a CSU 10 for a teleconsultation session. All other workstations 1' joining the teleconsultation work session could then be directed to the CSU 10 selected by the first workstation, for example by the CMSU 3 keeping track of the teleconsultation work groups.

The CMS 3 can host a communication program, for example a chat application or an e-phone, which could be used by both of the two users at the two remote workstations 1 and 1' for communicating with each other.

It is also conceivable that the CMSU 3 provides the communication platform instead of the CSU 10, 10'. In this case no separate CSU 10, 10' is required. However having at least one separate CSU 10, 10' has the advantage of relieving the CMSU 3, which is particularly advantageous if many users are connected to the CMSU 3 at the same time.

It is further conceivable to provide a separate communication channel between the participants of the teleconsultation session, such as, for example, a conventional telephone connection, a radio connection, or any other wireless sender-receiver means. Also, an existing software application or protocol could be used for realizing a communication over the Internet, for example via an existing chat program allowing the exchange of text messages, such as MSN Messenger, or an existing e-phone such as Skype, or a file transfer protocol application.

Preferably, the method further comprises allowing the digitized microscope slide 200 to be annotated at the first workstation 1, and transmitting the annotations to the second workstation 1' over the CSU 10, and vice versa. This can be done for example by creating an annotation file for the viewer program and transmitting the annotation file. Alternatively, if no CSU 10 is provided the annotations could be transmitted via other communication channels, for example the CMSU 3 or any existing file transfer program (e.g. the ones incorporated in conventional chat programs and e-phones). For the sake of simplicity from here on annotation management will be presented with reference to a CSU 10. Nevertheless, it is to be appreciated that the functions and services of the CSU 10 can be performed by other programs or units as well.

Transmitting the annotations enables the user at the second workstation 1' to view the annotations made at the first workstation 1, and vice versa, even if the two workstations 1, 1' are connected to different DSUs 2, 2'. If the two workstations are connected to a common DSU for accessing the selected digitized microscope slide 200, then it is also conceivable that the annotations be made directly on the common DSU 2 allowing the second user to view them from there.

Preferably the method also comprises saving the annotations on both DSUs 2, 2'. This could be achieved over communication lines 102 and 102' via the CSU 10, which could transmit all of the annotations made during the teleconsultation session to the respective DSUs 2, 2'. The annotations could be saved as part of the original digitized microscope slide 200 or separately, for example under the name of one of the users or in a folder dedicated to the teleconsultation session along with any extra notes or files that were created during the session. The annotations can relate to the whole of the digitized microscope slide 200 or to specific files, composite images 220, 221, image tiles 210, 211, 212, etc. comprised by the digitized microscope slide 200.

An advantage of the system 100 according to the invention is that the important data traffic takes place between the workstations 1 and 1' and the respective DSUs 2 and 2' over the communication lines 12 and 12' respectively. The CMSU 3 can optionally serve as an intermediate for communication between the two workstations 1 and 1' or it can be relieved from this function by a separate CSU 10.

Figure 4:
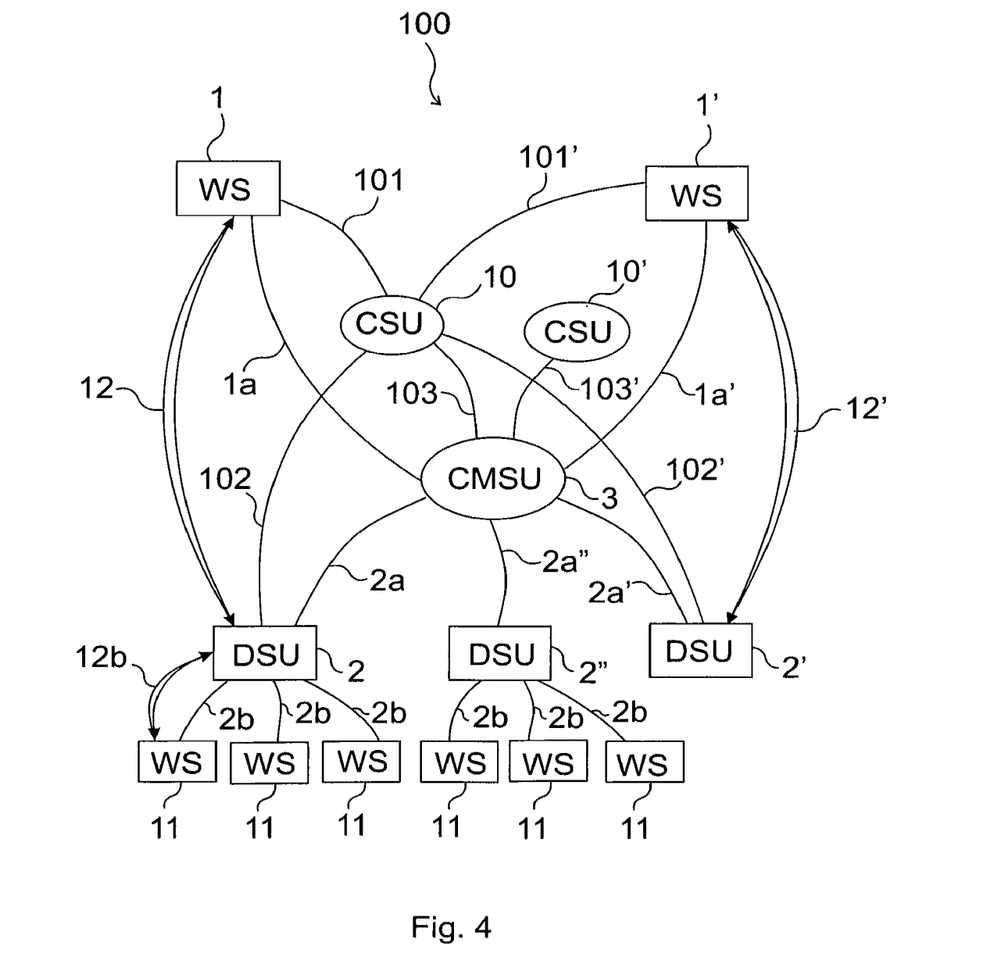
FIG. 4 is a block diagram illustrating the operation of an alternative system incorporating an indirect peer-to-peer network structure according to the invention.

FIG. 4 illustrates the operation of a second exemplary embodiment of a system 110 according to the invention.

The system 110 is basically identical to the system 100 depicted in FIG. 1, the main difference being that some of the DSUs 2, 2" are connected to a plurality of workstations 11 via communication lines 2b. It should be noted that any number of workstations 11 can be connected to a single DSU 2, 2", and any number of DSUs 2, 2" can be in connection with one or more workstations 11, while other DSUs 2' may not be in connection with any workstations 11.

The workstations 11 can be any kind of workstations storing one or more digitized microscope slides 200 that are registered on the respective DSU 2, 2" and are accessible via this DSU 2, 2". Notwithstanding, the DSUs 2, 2" can be storing digitized microscope slides 200, too. Slide information of the digitized microscope slides 200 stored in the workstations 11 are also registered on the CMSU 3 (along with the ones stored in the DSUs 2, 2', 2") and may be listed or searched as explained in connection with the system 100. The digitized microscope slides 200 stored in the workstations 11 preferably appear as being stored in one of the DSUs 2, 2", thus, when a user at a remote workstation 1 wishes to access such a digitized microscope slide 200 a similar procedure can take place as described for the system 100. After selecting a digitized microscope slide 200 from a list provided by the CMSU 3 the workstation 1 can connect to a DSU 2 storing the selected slide 200 or being connected to a workstation 11 storing the selected slide 200. Only the latter case will be discussed in further detail as in the former case accessing the selected slide 200 can take place in the same way as described for system 100.

If the digitized microscope slide 200 selected by a user at a first remote workstation 11 is stored in a second workstation 11 connected to the DSU 2, the DSU 2 uploads the digitized microscope slide 200 (all or only the parts requested by the first workstation 1) over communication line 12b and transmits them to the first workstation 1 over communication line 12. It is also possible that the DSU 2 connects the two workstations 1 and 11 with each other having the advantage that further data transfer can take place directly between the two workstations 1, 11 (direct peer-to-peer communication). However, the latter implies configuring the firewalls at the two workstations 1 and 11 to allow the necessary data exchange, which might be considerably difficult if local security regulations do not permit communication with remote workstations. For example, the workstations 11 in a hospital's local network might not be accessible by other workstations 1 outside of the hospital's network. In this case the hospital's server could serve as the DSU 2, allowing the file exchange between the two workstations 1 and 11 through uploading the required files from the second workstation 11 and transmitting them over to the first workstation 1 (indirect peer-to-peer communication).

In the exemplary embodiment depicted in FIG. 4 a third workstation 1' is connected to a second DSU 2' storing the same selected digitized microscope slide 200 as the one stored in the second workstation 11 and made accessible to the first workstations 1 via the first DSU 2. Teleconsultation can take place between the first and third workstations 1 and 1' via the CSU 10 as discussed earlier.

It is to be appreciated that the first and third workstations 1 and 1' may also be storing digitized microscope slides 200 that can be accessible by other workstations via an interposed DSU 2, 2', 2". The workstations 11 may also connect to the CMSU 3 for accessing other digitized microscope slides 200 stored in other DSUs 2, 2', 2" or workstations 11.

The above-described embodiments are intended only as illustrative examples and not to be considered as limiting the invention in any way. Various modifications will be apparent to a person skilled in the art without departing from the scope of protection defined by the attached claims.

What is claimed is:

1. A method for accessing a slide from a plurality of digitized microscope slides from a remote workstation, wherein the plurality of digitized microscope slides are accessible via a plurality of data station units (DSU), said method comprising:
providing a central management station unit (CMSU) connected to a communication network for storing slide information of the plurality of digitized microscope slides,
allowing the workstation to connect to the CMSU via the communication network;
providing at least a part of the slide information of the plurality of digitized microscope slides to the workstation;
allowing the workstation to select a digitized microscope slide based on the provided slide information; and
allowing for a direct connection over the communication network between the remote workstation and a DSU enabling access to the selected digitized microscope slide slide by providing said remote workstation with information about the DSUs enabling access to the selected digitized microscope slide and selecting a DSU depending on the provided information, wherein said selection of a DSU comprises testing the communication bitrate between the workstation and a DSU enabling access to the selected digitized microscope slide and selecting a DSU depending on the obtained communication bitrates.

2. The method according to claim 1, wherein the slide information comprises at least one of the following: slide name, slide size, slide attributes, slide location, slide path, information identifying the DSU, information relating to a specimen on the slide, SNOMED code, preview image of the slide, information relating to the proprietor of the slide.

3. The method according to claim 1, comprising searching the slide information stored in the CMSU based on a search criteria provided by the remote workstation and providing the slide information corresponding to the search criteria to the remote workstation.

4. The method according to claim 1, comprising transmitting from the DSU to the workstation at least a part of the selected digitized microscope slide, annotating the digitized microscope slide at the workstation, and transmitting back the annotations to the DSU.

5. The method according to claim 1, comprising providing user identification means for a user at the remote workstation by the CMSU and verifying the user identification means when the remote workstation requests data from the DSU enabling access to the selected digitized microscope slide.

6. The method according to claims 5, wherein the verification comprises the following steps:
transmitting the user identification means from the DSU to the CMSU;
requesting the verification of the user identification means.

7. The method according to claim 1, comprising allowing a second workstation to connect to the CMSU and allowing for a communication between the second workstation and a DSU enabling access to the digitized microscope slide selected by the first workstation.

8. The method according to claim 7, comprising providing an intermediate communication means between the first and second remote workstations.

9. The method according to claim 8, wherein the intermediate communication means is selected from a group comprising, the CMSU, a communication station unit (CSU), a telephone, a wireless sender-receiver means, an e-phone, an Internet chat program, a file exchange program.

10. The method according to claim 8, comprising transmitting annotations of the selected digitized microscope slide made at one of the workstations to the other workstation.

11. The method according to claim 7, comprising transmitting annotations of the selected digitized microscope slide made at one of the workstations to the DSU providing the selected digitized microscope slide to the first and second workstations.

12. The method according to claim 7, comprising allowing the second workstation to connect to a second DSU being different from the first DSU providing the selected digitized microscope slide to the first workstation, the second DSU enabling access to a same digitized microscope slide as selected by the first workstation.

13. The method according to claim 1, wherein the communication network is selected from a group comprising Internet, Intranet, LAN, wireless LAN and wireless WAN.

14. A method for accessing a slide from a plurality of digitized microscope slides from a remote work station, each of said digitized microscope slides comprising sets of image tiles of a microscope specimen slide and aligning information for aligning the image tiles of a set to form a composite image of the specimen slide at a given magnification, wherein the plurality of digitized microscope slides are accessible via a plurality of data station units (DSU), said method comprising:
providing a central management station unit (CMSU) connected to a communication network for storing slide information of the plurality of digitized microscope slides,
allowing the workstation to connect to the CMSU via the communication network;
providing at least a part of the slide information of the plurality of digitized microscope slides to the workstation;
allowing the workstation to select a digitized microscope slide based on the provided slide information;
allowing for a direct connection over the communication network between the remote workstation and a DSU enabling access to the selected digitized microscope slide;
allowing the workstation to request one or more image tiles of a given set from the DSU enabling access to the digitized microscope slide;
transmitting said requested image tiles and respective aligning information;
providing a viewer program at the remote workstation for aligning the transmitted image tiles using the transmitted aligning information and for displaying a region of the composite image of the microscope specimen slide at a given magnification using the aligned image tiles; and also
calibrating said viewer program by
displaying a calibration line of a given number of pixels by the viewer program;
allowing a user to input a value of a measured length of the calibration line;
calculating a display magnification from the measured length; and
using the display magnification for calculating a corrected magnification upon request of a given magnification.

15. The method according to claim 14, wherein the viewer program is configured to request adjacent image tiles of the same magnification of a displayed region of the microscope specimen slide from the DSU when a user scrolls out of the displayed region.

16. The method according to claim 14, wherein the viewer program is configured to request image tiles of another magnification when a user zooms in or out of the displayed slide region.

17. The method according to claim 14, wherein the viewer program is configured to cache the transmitted image tiles for use when displaying the same slide region at the same magnification again.

18. The method according to claim 14, comprising annotating the selected digitized microscope slide via the viewer program and transmitting the annotation back to the DSU.

19. The method according to claim 14, comprising using the calculated corrected magnification for re-scaling image tiles of a requested given magnification.

20. The method according to claim 14, comprising using the calculated corrected magnification for selecting a magnification for requesting image tiles from the DSU.

21. The method according to claim 14, comprising using the calculated corrected magnification for selecting a magnification for requesting image tiles from the DSU and re-scaling image tiles of the selected magnification to match the calculated corrected magnification.

22. A system for accessing a slide from a plurality of digitized microscope slides from a remote workstation connected to a communication network, each of said digitized microscope slides comprising sets of image tiles of a microscope specimen slide and aligning information for aligning the image tiles of a set to form a composite image of the specimen slide at a given magnification, said remote workstation being provided with a viewer program, said viewer program being configured to
request image tiles of a given region of the specimen slide at a given magnification and aligning information;
align the image tiles using the aligning information;
display the aligned image tiles;
display a calibration line of a given number of pixels;
allow a user to input a value of a measured length of the calibration line;
calculate a display magnification from the measured length; and
use the display magnification for calculating a corrected magnification upon request of a given magnification;
said system comprising:
a plurality of data station units (DSU) connected to the communication network and each having access to at least one of the plurality of digitized microscope slides;
a central management station unit (CMSU) connected to the communication network and configured to:

obtain slide information of the plurality of digitized microscope slides from the plurality of DSUs;

provide the remote workstation with at least part of the slide information over the communication network;

allow the remote workstation to select a digitized microscope slide based on the provided slide information; and allow for a direct connection over the communication network between the remote workstation and a DSU having access to the selected digitized microscope slide.

23. The system according to claim 22, wherein the CMSU comprises a virtual library comprising the slide information of the plurality of digitized microscope slides and further comprises a search tool for searching within the virtual library.

24. The system according to claim 22, wherein slide information comprises at least one of the following: slide name, slide size, slide attributes, slide location, slide path, information identifying the DSU, information relating to a specimen on the slide, SNOMED code, preview image of the slide, information relating to the proprietor of the slide.

25. The system according to claim 22, wherein the viewer program is configured to use the calculated corrected magnification for re-scaling image tiles of a requested given magnification.

26. The system according to claim 22, wherein the viewer program is configured to use the calculated corrected magnification for selecting a magnification for requesting image tiles from the DSU.

27. The system according to claim 22, wherein at least one DSU is connected to at least one workstation storing at least one digitized microscope slide, the digitized microscope slide being accessible by the DSU, and the DSU being configured to provide the remote workstation with at least part of the digitized microscope slide upon request.

28. The system according to claim 22, wherein at least one DSU is connected to at least one workstation storing at least one digitized microscope slide, and the DSU being configured to allow for a direct connection between the remote workstation and the at least one workstation connected to the DSU upon request for said at least one digitized microscope slide.

29. The system according to claim 22, further comprising at least one communication station unit (CSU) for providing an intermediate communication means between the remote workstation and a DSU having access to a selected digitized microscope slide.

30. The system according to claim 22, wherein the communication network comprises at least one of a group comprising Internet, Intranet and LAN.

* * * * *